US006987178B2

(12) United States Patent
Turner, Jr. et al.

(10) Patent No.: US 6,987,178 B2
(45) Date of Patent: *Jan. 17, 2006

(54) HUMAN UNCOUPLING PROTEINS AND POLYNUCLEOTIDES ENCODING THE SAME

(75) Inventors: C. Alexander Turner, Jr., The Woodlands, TX (US); Brian Mathur, The Woodlands, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 302 days.

This patent is subject to a terminal disclaimer.

(21) Appl. No.: 10/165,813

(22) Filed: Jun. 7, 2002

(65) Prior Publication Data

US 2005/0181500 A1 Aug. 18, 2005

Related U.S. Application Data

(63) Continuation of application No. 09/501,558, filed on Feb. 9, 2000, now Pat. No. 6,403,784.

(60) Provisional application No. 60/158,458, filed on Oct. 8, 1999, provisional application No. 60/119,228, filed on Feb. 9, 1999.

(51) Int. Cl.
*C07H 21/04* (2006.01)
*C07H 21/02* (2006.01)
*C12P 21/06* (2006.01)
*C07K 14/00* (2006.01)
*C07K 1/00* (2006.01)

(52) U.S. Cl. .................... 536/23.5; 536/23.1; 435/69.1; 435/320.1; 435/252.3; 435/455; 530/350; 530/300

(58) Field of Classification Search .............. 536/23.1, 536/23.5; 435/69.1, 252.3, 320.1, 455; 530/350, 530/300; 514/44
See application file for complete search history.

(56) References Cited

U.S. PATENT DOCUMENTS

| 4,190,496 A | 2/1980 | Rubenstein et al. |
| 4,215,051 A | 7/1980 | Schroeder et al. |
| 4,376,110 A | 3/1983 | David et al. |
| 4,683,202 A | 7/1987 | Mullis |
| 4,873,191 A | 10/1989 | Wagner et al. |
| 4,946,778 A | 8/1990 | Ladner et al. |
| 5,075,217 A | 12/1991 | Weber |
| 5,364,759 A | 11/1994 | Caskey et al. |
| 5,399,346 A | 3/1995 | Anderson et al. |
| 5,625,048 A | 4/1997 | Tsien et al. |
| 5,702,902 A | 12/1997 | Tartaglia |
| 5,741,666 A | 4/1998 | Tartaglia |
| 5,780,280 A | 7/1998 | Lebkowski et al. |
| 5,824,544 A | 10/1998 | Armentano et al. |
| 5,827,703 A | 10/1998 | Debs et al. |
| 5,830,727 A | 11/1998 | Wang et al. |
| 5,837,458 A | 11/1998 | Minshull et al. |
| 5,840,710 A | 11/1998 | Lee et al. |
| 5,843,742 A | 12/1998 | Natsoulis et al. |
| 5,846,528 A | 12/1998 | Podsakoff et al. |
| 5,853,975 A | 12/1998 | Tartaglia |
| 5,858,740 A | 1/1999 | Finer et al. |
| 6,403,784 B1 * | 6/2002 | Turner et al. ............... 536/23.5 |
| 2003/0073623 A1 * | 4/2003 | Drmanac et al. ............. 514/12 |

FOREIGN PATENT DOCUMENTS

| WO | WO98/03243 | 1/1998 |
| WO | WO 9831396 | 7/1998 |
| WO | WO 9845313 | 10/1998 |
| WO | WO 9845438 | 10/1998 |
| WO | WO98/50542 | 11/1998 |

OTHER PUBLICATIONS

Hyseq Inc., US20030073623A1, sequence alignment.*
Bird et al, 1988, "Single-Chain Antigen-Binding Proteins", Science 242:423-426.
Bitter et al. 1987, "Expression and Secretion Vectors for Yeast". Methods in Enzymology 153:516-544.
Butler, J.E., 1981, "The Amplified ELISA: Principles of and Applications for the Comparative Quantitation of Class and Subclass Antibodies and the Distribution of Antibodies and Antigens in Biochemical Separates", Meth. Enzymol. 73: 482-523.
Colbere-Garapin et al, 1981, "A New Dominant Hybrid Selective Marker for Higher Eukaryotic Cells", J. Mol. Biol. 150:1-14.
Cote et al, 1983, "Generation of human monoclonal antibodies reactive with cellular antigens", Proc. Natl. Acad. Sci. USA 80:2026-2030.
Gautier et al, 1987, "α-DNA IV:α-anomeric and β-anomeric letrathymidylates covalently linked to intercalating oxazolopyridocarbazole. Synthesis, physiochemical properties and poly (rA) binding", Nucleic Acids Research 15(16): 6625-6641.
Gordon, 1989, "Transgenic Animals", Intl. Rev. Cytol. 115: 171-229.
Greenspan et al, 1993, "Idiotypes: structure and immunogenicity", FASEB Journal 7:437-444.
Gu et al, 1994, "Deletion of a DNA Polymerase βGene Segment in T Cells Using Cell Type-Specific Gene Targeting", Science 265:103-106.

(Continued)

*Primary Examiner*—Jon Weber
*Assistant Examiner*—Rita Mitra

(57) ABSTRACT

The present invention relates to methods and compositions for the treatment of biological disorders regulatable by the controlled expression or inhibition of the described uncoupling proteins (UCPs).

6 Claims, No Drawings

OTHER PUBLICATIONS

Inoue et al, 1987, "Sequence-dependent hydrolysis of RNA using modified oligonucleotide splints and R Nase H", FEBS Letters 215(2):327-330.

Inoue et al, 1987, "Synthesis and hybridization studies on two complementary nona(2'-O-methyl)ribonucleotides", Nucleic Acids Research 15(15):6131-6149.

Inouye & Inouye, 1985, "Up-promoter mutations in the lpp gene of *Escherichia coli*", Nucleic Acids Research 13(9): 3101-3110.

Janknecht et al, 1991, "Rapid and efficient purification of native histidine-tagged protein expressed by recombinant vaccinia virus", Proc. Natl. Acad. Sci. USA 88:8972-8976.

Kohler and Milstein, 1975, "Continuous cultures of fused cells secreting antibody of predefined specificity", Nature 256:495-497.

Lakso et al, 1992, "Targeted oncogene activation by site-specific recombination in transgenic mice", Proc. Natl. Acad. Sci. USA 89:6232-6236.

Lavitrano et al, 1989, "Sperm Cells as Vectors for Introducing Foreign DNA into Eggs: Genetic Transformation of Mice", Cell 57:717-723.

Lo, 1983, "Transformation by Iontophoretic Microinjection of DNA: Multiple Integrations without Tandem Insertions", Mol. & Cell. Biology 3(10):1803-1814.

Logan et al, 1984, "Adenovirus tripartite leader sequence enhances translation of mRNAs late after infection", Proc. Natl. Acad. Sci. USA 81:3655-3659.

Lowy et al, 1980, "Isolation of Transforming DNA: Cloning the Hamster aprt Gene", Cell 22:817-823.

Miyajima et al, 1986, "Expression of murine and human granulocyte-macrophase colony-stimulating factors in *S. cerevisiae*: mutagenesis of the potential glycosvlation sites", EMBO J. 5:6. 1193-1197.

Mulligan & Berg, 1981, "Selection for animal cells that express the *Escherichia coli* gene coding for xanthine-guanine phosphoribosyltransferase", Proc. Natl. Acad. Sci. USA 78(4):2072-2076.

Neuberger et al, 1984, "Recombinant antibodies possessing novel effector functions", Nature 312:604-608.

Nisonoff, 1991, "Idiotypes: Concepts and Applications", J. of Immunology 147:2429-2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527-1531.

Platt, et al., 1994, "Independent Regulation of Adipose Tissue-specificity and Obesity Response of the Adipsin Promoter in Transgenic Mice", J. Biol. Chem. 269:28558-28562.

Ruther et al, 1983, "Easy identification of cDNA clones", EMBO Journal 2(10): 1791-1794.

Santerre et al, 1984, "Expression of prokaryotic genes for hygromycin B and G418 resistance as dominant-selection markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Smith et al, 1983, "Molecular Engineering of the Autographa californica Nuclear Polyhedrosis Virus Genome: Deletion Mutations within the Polyhedrin Gene", J. Virol. 46(2):584-593.

Stein et al, 1988, "Physiochemical properties of phosphorothioate oligodeoxynucleotides", Nucleic Acids Research 16(8):3209-3221.

Szybalska & Szybalski, 1962, "Genetics of Human Cell Lines, IV. DNA-Mediated Heritable Transformation of a Biochemical Trait", Proc. Natl. Acad. Sci. USA 48:2026.

Takeda et al, 1985, "Construction of chimaeric processed immunoglobulin genes containing mouse variable and human constant region sequences", Nature 314:452-454.

Thompson et al, 1989, "Germ Line Transmission and Expression of a Corrected HPRT Gene Produced by Gene Targeting in Embryonic Stem Cells", Cell 56:313-321.

Van Der Putten et al, 1985, "Efficient insertion of genes into the mouse germ line via retroviral vectors", Proc. Natl. Acad. Sci. USA 82:6148-6152.

Van Heeke & Schuster, 1989, "Expression of Human Asparagine Synthetase in *Escherichio coli*", J. Biol. Chem. 264:5503-5509.

Voller, A. et al, 1978, "Enzyme immunoassays with special reference to ELISA techniques", J. Clin. Pathol. 31:507-520.

Ward et al, 1989, "Binding activities of a repertoire of single immunoglobulin variable domains secreted from *Escherichia coli*", Nature 341:544-546.

Wigler et al, 1977, "Transfer of Purified Herpes Virus Thymidine Kinase Gene to Cultured Mouse Cells", Cell 11:223.

Wigler et al, 1980, "Transformation of mammalian cells with an amplifiable dominant-acting gene", Proc. Natl. Acad. Sci. USA 77(6):3567-3570.

Database Embl Nucleotide and Protein Sequences, 1998, XP002141168 Hinxton, GB, Soares_pregnant_uterus_NbHPU Homo sapiens cDNA clone, NCI-CGAP; National Cancer Institute, Cancer Genome Anatomy Project. Tumor Gene Index http://www.ncbi.nlm.nih.gov/ncicgap.

Database Embl Nucleotide and Protein Sequences, 1998, XP002141171, Hinxton, GB, Soares 2NbMT Mus musculus cDNA clone Image: 1265034, Mitochondrial Uncoupling Protein 2; mRNA sequence, Washington University School of Medicine.

Database Embl Nucleotide and Protein Sequences, 2000, XP002141172, Hinxton, GB, NCI_CGAP_Sub4 Homo sapiens cDNA clone, National Cancer Institute, Cancer Genome Anatomy Project (CGAP), Tumor Gene Index http://www.ncbi.nlm.nih.gov/ncicgap.

Database Embl Nucleotide and Protein Sequences, 2000, XP002141173, Hinxton, GB, Soares_NFL_T_GBC-S1 Homo sapiens cDNA clone, National Cancer Institute, Cancer Genome Anatomy Project (CGAP), Tumor Gene Index http://www.ncbi.nlm.nih.gov/ncicgap.

Mao et al, 1998, "UCP4, a novel brain-specific mitochondrial protein that reduces membrane potential in mammalian cells", Febs Letters 443(3):326-330.

Sanchis et al, 1998, "BMCP1, a Novel Mitochondrial Carrier with High Expression in the Central Nervous System of Humans and Rodents, and Respiration Uncoupling Activity in Recombinant Yeast", Journal of Biological Chemistry, 273(51):34611-34615.

\* cited by examiner

HUMAN UNCOUPLING PROTEINS AND POLYNUCLEOTIDES ENCODING THE SAME

The present application is a continuation of U.S. application Ser. No. 09/501,558 filed Feb. 9, 2000, now U.S. Pat. No. 6,403,784, issued Jun. 11, 2002, which claims the benefit of U.S. Provisional Application Ser. No. 60/119,228, filed Feb. 9, 1999, and U.S. Application Ser. No. 60/158,458, filed Oct. 8, 1999, each of which are herein incorporated by reference in their entirety.

1. INTRODUCTION

The present invention relates to the discovery, identification, and characterization of novel human polynucleotide sequences and the novel polypeptides encoded thereby. The invention encompasses the described polynucleotides, host cell expression systems, the encoded proteins or polypeptides, and fusion proteins and peptides derived therefrom, antibodies to the encoded proteins or peptides, and genetically engineered animals that lack functional forms of the genes encoding the disclosed sequences, over express the disclosed sequences, as well as antagonists and agonists of the proteins, along with other compounds that modulate the expression or activity of the proteins encoded by the disclosed sequences that can be used for diagnosis, drug screening, clinical trial monitoring, the treatment of physiological or behavioral disorders, or otherwise improving the quality of life.

2. BACKGROUND OF THE INVENTION

Uncoupling proteins (UCPs) are found in the mitochondria, but are encoded within the nucleus. In the mitochondria, UCPs uncouple, or regulate, the gradient that drives energy production in the cell/body. As such, UCPs effectively modulate the efficiency of energy production in the body, and hence body metabolism. Given the role of UCPs in the body, they are thought to be important targets for the study of thermogenesis, obesity, cachexia, and other metabolically related physiological functions, diseases, and disorders.

3. SUMMARY OF THE INVENTION

The present invention relates to the discovery, identification, and characterization of nucleotides that encode novel human UCPs, and the corresponding amino acid sequences encoded by the disclosed sequences. The novel human uncoupling proteins (NUCPs) described for the first time herein share structural relatedness with other mammalian uncoupling proteins and brain mitochondrial carrier proteins. The novel human nucleic acid sequences described herein encode proteins of 291 and 293 amino acids in length (see SEQ ID NOS:2 and 4).

A murine homologue of the described NUCPs has been identified and a "knockout" ES cell line has been produced using the methods described in U.S. application Ser. Nos. 08/942,806, herein incorporated by reference. Alternatively, such knockout cells and animals can be produced using conventional methods for generating genetically engineered animals and cells (see, for example, PCT Applic. No. PCT/US98/03243, filed Feb. 20, 1998, herein incorporated by reference). Accordingly, an additional aspect of the present invention includes knockout cells and animals having genetically engineered mutations in gene encoding the presently described NUCPs.

The invention encompasses the nucleotides presented in the Sequence Listing, host cells expressing such nucleotides, and the expression products of such nucleotides, and: (a) nucleotides that encode mammalian homologs of the described genes, including the specifically described NUCPs, and the NUCP products; (b) nucleotides that encode one or more portions of the NUCPs that correspond to functional domains, and the polypeptide products specified by such nucleotide sequences, including but not limited to the novel regions of any active domain(s); (c) isolated nucleotides that encode mutant versions, engineered or naturally occurring, of the described NUCPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of NUCP, or one of its domains (e.g., a transmembrane domain, accessory protein/self-association domain, etc.) fused to another peptide or polypeptide.

The invention also encompasses agonists and antagonists of NUCPs, including small molecules, large molecules, mutant NUCPs, or portions thereof that compete with or bind to native NUCPS, antibodies, and nucleotide sequences that can be used to inhibit the expression of the described NUCPs (e.g., antisense, ribozyme molecules, and gene or regulatory sequence replacement constructs) or to enhance the expression of the described NUCPs (e.g., expression constructs that place the described genes under the control of a strong promoter system), as well as transgenic animals that express a NUCP transgene, or "knockouts" (which can be conditional) that do not express functional NUCP.

Further, the present invention also relates to methods for using of the described NUCP products for the identification of compounds that modulate, i.e., act as agonists or antagonists, of NUCP expression and/or NUCP product activity. Such compounds can be used as therapeutic agents for the treatment of any of a wide variety of symptomatic representations of biological disorders or imbalances.

An additional embodiment of the present invention includes therapy and treatments mediated by NUCP gene delivery. Gene delivery can be to somatic or stem cells, and may be effected using viral (i.e., retrovirus, adeno-associated virus, etc.) or non-viral (i.e., cationic lipids, formulations using "naked" DNA, etc.) methods.

4. DESCRIPTION OF THE SEQUENCE LISTING AND FIGURES

The Sequence Listing provides the sequences of the NUCP polynucleotides, and the amino acid sequences encoded thereby.

5. DETAILED DESCRIPTION OF THE INVENTION

The NUCPs described for the first time herein are novel proteins that are expressed, inter alia, in gene trapped human cells, human lymph node or kidney cells, and/or ES cells. The NUCPs exert biological effect by regulating the efficiency of energy generation in the body with the result being that excess resources are converted to heat or are otherwise stored as fat, etc. Regulating the function of a NUCP product will effect NUCP-mediated processes with resulting effects on fat production and usage, superoxide generation and regulation, and all biological properties and functions that are tied to fatty acid metabolism. Because of these important roles, UCPs have been the focus of intense scientific scrutiny (see PCT Application No. PCT/EP98/02645, U.S. Pat. Nos. 5,853,975, 5,741,666 and 5,702,902 all of which are herein incorporated by reference in their entirety).

The present invention encompasses the use of the described NUCP nucleotides, NUCPs and NUCP peptides therefrom, as well as antibodies, preferably humanized monoclonal antibodies, or binding fragments, domains, or fusion proteins thereof, or antiidiotypic variants derived therefrom, that bind NUCP (which can, for example, also act as NUCP agonists or antagonists), other antagonists that inhibit binding activity or expression, or agonists that activate NUCP receptor activity or increase NUCP expression, in the diagnosis and/or treatment of disease.

In particular, the invention described in the subsections below encompasses NUCP polypeptides or peptides corresponding to functional domains of NUCPs, mutated, truncated or deleted NUCPs (e.g., NUCPs missing one or more functional domains or portions thereof), NUCP fusion proteins (e.g., where NUCP or a functional domain of NUCP is fused to an unrelated protein or peptide such as an immunoglobulin constant region, i.e., IgFc), nucleotide sequences encoding such products, and host cell expression systems that can produce such NUCP products.

The invention also encompasses antibodies and antiidiotypic antibodies (including Fab fragments), antagonists and agonists of the NUCP, as well as compounds or nucleotide constructs that inhibit expression of a NUCP gene (transcription factor inhibitors, antisense and ribozyme molecules, or gene or regulatory sequence replacement constructs), or promote expression of a NUCP (e.g., expression constructs in which a NUCP coding sequence is operatively associated with expression control elements such as promoters, promoter/enhancers, etc.). The invention also relates to host cells and animals genetically engineered to express a NUCP (or mutant variants thereof) or to inhibit or "knockout" expression of an animal homolog of a NUCP gene.

The NUCPs, NUCP peptides, and NUCP fusion proteins derived therefrom, NUCP nucleotide sequences, antibodies, antagonists and agonists can be useful for the detection of mutant NUCPs or inappropriately expressed NUCPs for the diagnosis of biological disorders (high blood pressure, obesity, etc.) and disease. The NUCP products or peptides, NUCP fusion proteins, NUCP nucleotide sequences, host cell expression systems, antibodies, antagonists, agonists and genetically engineered cells and animals can also be used for screening for drugs (or high throughput screening of combinatorial libraries) effective in the treatment of the symptomatic or phenotypic manifestations of perturbing the normal function of NUCP in the body. The use of engineered host cells and/or animals may offer an advantage in that such systems allow not only for the identification of compounds that bind to an endogenous NUCP, but can also identify compounds that facilitate or inhibit NUCP-mediated uncoupling.

Of particular interest are genetically engineered nucleotide constructs, or expression vectors, that encode NUCP products and derivatives (NUCP peptides, fusions, etc). Nucleotide constructs encoding such NUCP products and derivatives can be used to genetically engineer host cells to express such products in vivo; these genetically engineered cells function as "bioreactors" in the body delivering a continuous supply of a NUCP product, NUCP peptide, or NUCP fusion protein to the body. Nucleotide constructs encoding functional NUCPs, mutant NUCPs, as well as antisense and ribozyme molecules can also be used in "gene therapy" approaches for the modulation of NUCP expression. Thus, the invention also encompasses pharmaceutical formulations and methods for treating biological disorders.

Therapeutic gene delivery of the described NUCP nucleotides can be effected by a variety of methods. For example, methods of retroviral human gene therapy are described in, inter alia, U.S. Pat. Nos. 5,399,346 and 5,858,740; adenoviral vectors for gene therapy/delivery are described in U.S. Pat. No. 5,824,544; adeno-associated viral vectors are described in U.S. Pat. Nos. 5,843,742, 5,780,280, and 5,846,528; herpes virus vectors are described in U.S. Pat. No. 5,830,727, and other vectors and methods of nonvirally (e.g., polynucleotides that are not encapsulated by viral capsid protein, "naked" DNA, or DNA formulated in lipid or chemical complexes) introducing foreign genetic material of recombinant origin into a host mammalian, and preferably human, cell are described in U.S. Pat. Nos. 5,827,703 and 5,840,710 all of which are herein incorporated by reference in their entirety. When the above methods are applied to selectively express or inhibit the expression of a NUCP in tumor/diseased cells, the described methods and compositions can be used as chemotherapeutic agents for the treatment of cancer and other diseases and disorders.

Various aspects of the invention are described in greater detail in the subsections below.

5.1. The NUCP Polynucleotides

The cDNA sequences (SEQ ID NOS:1 and 3) and deduced amino acid sequences (SEQ ID NOS:2 and 4) of the described NUCPs are presented in the Sequence Listing. The NUCP cDNA sequences were obtained from human lymph node, kidney, and fetal brain cDNA libraries (Edge Biosystems, Gaithersburg, Md.) using probes and/or primers generated from gene trapped sequence tags and a human homolog of the described NUCPs. RT-PCR analysis indicated that expression of the described NUCPs can be detected in, inter alia, human cerebellum, spinal cord, thymus, spleen, lymph node, bone marrow, trachea, lung, kidney, fetal liver, prostate, testis, thyroid, salivary gland, stomach, heart, uterus, and mammary gland, with particularly strong expression in kidney, adrenal gland, and skeletal muscle. The above expression studies were largely verified by Northern analysis that also detected particularly strong expression in human skeletal muscle, heart, adrenal gland, and kidney.

The NUCPs of the present invention include: (a) the human DNA sequences presented in the Sequence Listing and additionally contemplates any nucleotide sequence encoding a contiguous and functional NUCP open reading frame (ORF) that hybridizes to a complement of the DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NUCP product. Functional equivalents of a NUCP include naturally occurring NUCPs present in other species, and mutant NUCPs whether naturally occurring or engineered. The invention also includes degenerate variants of the disclosed sequences.

The invention also includes nucleic acid molecules, preferably DNA molecules, that hybridize to, and are therefore the complements of, the described NUCP nucleotide sequences. Such hybridization conditions may be highly stringent or less highly stringent, as described above. In instances wherein the nucleic acid molecules are deoxyqligonucleotides ("DNA oligos"), such molecules are particularly about 16 to about 100 bases long, about 20 to about 80, or about 34 to about 45 bases long, or any variation or combination of sizes represented therein that incorporate a contiguous region of sequence first disclosed in the present Sequence Listing. Such oligonucleotides can be used in conjunction with the polymerase chain reaction (PCR) to screen libraries, isolate clones, and prepare cloning and sequencing templates, etc. Alternatively, the NUCP oligonucleotides can be used as hybridization probes for screening libraries or assessing gene expression patterns (particularly using a micro array or high-throughput "chip" format). Chip applications can involve a series of the described NUCP oligonucleotide sequences, or the complements thereof, can be used to represent all or a portion of the described NUCP sequences. The oligonucleotides, typically between about 16 to about 40 (or any whole number within the stated range) nucleotides in length may partially overlap each other and/or the NUCP sequence may be represented using oligonucleotides that do not overlap. Accordingly, the described NUCP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NUCP gene antisense molecules, useful, for example, in NUCP gene regulation (for and/or as antisense primers in amplification reactions of NUCP gene nucleic acid sequences). With respect to NUCP gene regulation, such techniques can be used to regulate biological functions. Further, such sequences may be used as part of ribozyme and/or triple helix sequences that are also useful for NUCP gene regulation.

Additionally, the antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and a hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NUCP nucleotide probes can be used to screen a human genomic library using appropriately stringent conditions or by PCR. The identification and characterization of human genomic clones is helpful for identifying polymorphisms, determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NUCP gene homolog can be isolated from nucleic acid of the organism of interest by performing PCR using two degenerate or "wobble" oligonucleotide primer pools designed on the basis of amino acid sequences within the NUCP product disclosed herein. The template for the reaction may be total RNA, mRNA, and/or cDNA obtained by reverse transcription of mRNA prepared from, for example, human or non-human cell lines or tissue, such as choroid plexus, known or suspected to express a NUCP gene allele.

The PCR product may be subcloned and sequenced to ensure that the amplified sequences represent the sequence of the desired NUCP gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express a NUCP gene, such as, for example, brain tissue). A reverse transcription (RT) reaction may be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment may easily be isolated. For a review of cloning strategies which may be used, see e.g., Sambrook et al., 1989, supra.

A cDNA of a mutant NUCP gene may be isolated, for example, by using PCR. In this case, the first cDNA strand may be synthesized by hybridizing an oligo-dT oligonucleotide to mRNA isolated from tissue known or suspected to be expressed in an individual putatively carrying a mutant NUCP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NUCP allele to that of the normal NUCP allele, the mutation(s) responsible for the loss or alteration of function of the mutant NUCP gene product can be ascertained.

Alternatively, a genomic library can be constructed using DNA obtained from an individual suspected of or known to carry the mutant NUCP allele (e.g., a person manifesting a NUCP-associated phenotype such as, for example, obesity, high blood pressure, etc.), or a cDNA library can be constructed using RNA from a tissue known, or suspected, to express a mutant NUCP allele. The normal NUCP gene, or any suitable fragment thereof, can then be labeled and used as a probe to identify the corresponding mutant NUCP allele in such libraries. Clones containing the mutant NUCP gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant NUCP allele in an individual suspected of or known to carry such a mutant allele. In this manner, gene products made by the putatively mutant tissue may be expressed and screened using standard antibody screening techniques in conjunction with antibodies raised against the normal NUCP product as described below (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NUCP fusion proteins, such as, for example, AP-NUCP or NUCP-AP fusion proteins. In cases where a NUCP mutation results in an expressed gene product with altered function (e.g., as a result of a missense or a frameshift mutation), a polyclonal set of antibodies to NUCP are likely to cross-react with the mutant NUCP gene product. Library clones detected via their reaction with such labeled antibodies can be purified and subjected to sequence analysis according to methods well known in the art.

The invention also encompasses nucleotide sequences that encode mutant NUCPs, peptide fragments of NUCPs, truncated NUCPs, and NUCP fusion proteins. These include, but are not limited to nucleotide sequences encoding the mutant NUCPs described below; polypeptides or peptides corresponding to one or more domains of NUCP or portions of these domains; truncated NUCPs in which one or more of the domains is deleted, or a truncated nonfunctional NUCPs. Nucleotides encoding fusion proteins may include, but are not limited to, full length NUCP sequences, truncated NUCPS, or nucleotides encoding peptide fragments of a NUCP fused to an unrelated protein or peptide, such as for example, a NUCP domain fused to an Ig Fc domain which increases the stability and half life of the resulting fusion protein (e.g., NUCP-Ig) in the bloodstream; or an enzyme such as a fluorescent protein or a luminescent protein which can be used as a marker.

The invention also encompasses (a) DNA vectors that contain any of the foregoing NUCP coding sequences and/or their complements (i.e., antisense); (b) DNA expression vectors that contain any of the foregoing NUCP coding sequences operatively associated with a regulatory element that directs the expression of the coding sequences; (c) genetically engineered host cells that contain any of the foregoing NUCP coding sequences operatively associated with a regulatory element that directs the expression of the coding sequences in the host cell; and (d) genetically engineered host cells that express an endogenous NUCP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus hCMV immediate early gene, regulatable, viral (particularly retroviral LTR promoters) the early or late promoters of SV40 adenovirus, the lac system, the trp system, the tet system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

5.2. The NUCPS and NUCP Polypeptides and Peptides Derived Therefrom

The NUCPs, NUCP polypeptides, NUCP peptide fragments, mutated, truncated, or deleted forms of a NUCP, and/or NUCP fusion proteins can be prepared for a variety of uses, including but not limited to the generation of antibodies, as reagents in diagnostic assays, the identification of other cellular gene products related to a NUCP, as reagents in assays for screening for compounds that can be as pharmaceutical reagents useful in the therapeutic treatment of mental, biological, or medical disorders and disease.

The Sequence Listing discloses the amino acid sequences encoded by the described NUCP polynucleotides. The NUCP sequences both display initiator methionines that are present in a DNA sequence context consistent with a translation initiation site (Kozak sequence).

The NUCP sequences of the invention include the nucleotide and amino acid sequences presented in the Sequence Listing as well as analogues and derivatives thereof. Further, corresponding NUCP homologues from other species are encompassed by the invention. In fact, any NUCP protein encoded by the NUCP nucleotide sequences described above are within the scope of the invention as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NUCP encoded by the presently described nucleotide sequences, as judged by any of a number of criteria, including, but not limited to, the ability to partition into the mitochondria, or other cellular membrane structure, and effect uncoupling activity, change in cellular metabolism (e.g., ion flux, tyrosine phosphorylation, etc.), or change in phenotype when the NUCP equivalent is expressed at similar levels, or mutated, in an appropriate cell type (such as the amelioration, prevention or delay of a biochemical, biophysical, or overt phenotype). Functional equivalents of a NUCP include naturally occurring NUCPs present in other species and mutant NUCPs whether naturally occurring or engineered (by site directed mutagenesis, gene shuffling, directed evolution as described in, for example, U.S. Pat. No. 5,837,458). The invention also includes degenerate nucleic acid variants and splice variant of the disclosed NUCP polynucleotide sequence.

Additionally contemplated are polynucleotides encoding NUCP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

Functionally equivalent NUCP proteins include, but are not limited to, additions or substitutions of amino acid residues within the amino acid sequence encoded by the NUCP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to NUCP encoding DNA (using random mutagenesis techniques well known to those skilled in the art) and the resulting mutant NUCPs tested for activity, site-directed mutations of the NUCP coding sequence can be engineered (using site-directed mutagenesis techniques well known to those skilled in the art) to generate mutant NUCPs with increased function, e.g., higher receptor binding affinity, decreased function, and/or increased physiological half-life, and increased signal transduction triggering. One starting point for such analysis is by aligning the disclosed human sequences with corresponding gene/protein sequences from, for example, other mammals in order to identify amino acid sequence motifs that are conserved between different species. Non-conservative changes can be engineered at variable positions to alter function, signal transduction capability, or both. Alternatively, where alteration of function is desired, deletion or non-conservative alterations of the conserved regions (i.e., identical amino acids) can be engineered. For example, deletion or non-conservative alterations (substitutions or insertions) of the various conserved transmembrane domains.

Other mutations to a NUCP coding sequence can be made to generate NUCPs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions, of any one or more of the glycosylation recognition sequences which occur in an ECD (N-X-S or N-X-T), and/or an amino acid deletion at the second position of any one or more such recognition sequences in an ECD will prevent glycosylation of the NUCP at the modified tripeptide sequence. (See, e.g., Miyajima et al., 1986, EMBO J. 5(6):1193–1197).

Peptides corresponding to one or more domains of a NUCP, truncated or deleted NUCPs, as well as fusion proteins in which a full length NUCP, a NUCP peptide, or a truncated NUCP is fused to an unrelated protein, are also within the scope of the invention and can be designed on the basis of the presently disclosed NUCP gene nucleotide and NUCP amino acid sequences. Such fusion proteins include, but are not limited to, Ig Fc fusions which stabilize a NUCP protein, or NUCP peptides, and prolong half-life in vivo; or fusions to any amino acid sequence that allows the fusion protein to be anchored to the cell membrane; or fusions to an enzyme, fluorescent protein, or luminescent protein which provide a marker function.

While the NUCPs and NUCP peptides can be chemically synthesized (e.g., see Creighton, 1983, Proteins: Structures and Molecular Principles, W. H. Freeman & Co., N.Y.), large polypeptides derived from a full length NUCP can be advantageously produced by recombinant DNA technology using techniques well known in the art for expressing nucleic acids containing NUCP gene sequences and/or coding sequences. Such methods can be used to construct expression vectors containing the described NUCP nucleotide sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA corresponding to all or a portion of a transcript encoded by a NUCP gene sequence can be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems can be utilized to express the NUCP-encoding nucleotide sequences of the invention. Where a NUCP peptide or polypeptide is a soluble derivative (e.g., NUCP peptides corresponding to an ECD; truncated or deleted NUCP in which a TM and/or CD are deleted, etc.) the peptide can be recovered from the host cell in cases where the NUCP peptide or polypeptide is not secreted, and from the culture media in cases where the NUCP peptide or polypeptide is secreted by the cells. However, such expression systems also encompass engineered host cells that express a NUCP, or a functional equivalent thereof, in situ, i.e., anchored in the cell membrane. Purification or enrichment of a NUCP from such expression systems can be accomplished using appropriate detergents and lipid micelles and methods well known to those skilled in the art. However, such engineered host cells themselves may be used in situations where it is important not only to retain the structural and functional characteristics of a NUCP, but to assess biological activity, e.g., in drug screening assays.

The expression systems that can be used for purposes of the invention include but are not limited to microorganisms such as bacteria (e.g.,. E. coli, B. subtilis) transformed with recombinant bacteriophage DNA, plasmid DNA or cosmid DNA expression vectors containing NUCP nucleotide sequences; yeast (e.g., Saccharomryces, Pichia) transformed with recombinant yeast expression vectors containing NUCP nucleotide sequences; insect cell systems infected with recombinant virus expression vectors (e.g., baculovirus) containing NUCP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NUCP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NUCP product being expressed. For example, when a large quantity of such a protein is to be produced for the generation of pharmaceutical compositions of or containing NUCP, or for raising antibodies to a NUCP, vectors that direct the expression of high levels of fusion protein products that are readily purified may be desirable. Such vectors include, but are not limited, to the E. coli expression vector pUR278 (Ruther et al., 1983, EMBO J. 2:1791), in which a NUCP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in Spodoptera frugiperda cells. The NUCP gene coding sequence may be cloned individually into non-essential regions (for example the polyhedrin gene) of the virus and placed under control of an AcNPV promoter (for example the polyhedrin promoter). Successful insertion of the NUCP gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NUCP gene nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing NUCP in infected hosts (e.g., See Logan & Shenk, 1984, Proc. Natl. Acad. Sci. USA 81:3655–3659). Specific initiation signals may also be required for efficient translation of NUCP transcripts. These signals include the ATG initiation codon and adjacent sequences. In cases where an entire NUCP gene or cDNA, including its own initiation codon and adjacent sequences, is inserted into the appropriate expression vector, no additional translational control signals may be needed (for example an independent ribosome entry site, or IRES, site). However, in cases where only a portion of a NUCP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can have a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the presently described NUCPs can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express a NUCP. Such engineered cell lines may be particularly useful in screening and evaluation of compounds that affect the endogenous activity of the NUCP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^{31}$, $hgprt^{31}$ or $aprt^{31}$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

NUCP products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NUCP transgenic animals.

Any technique known in the art may be used to introduce a NUCP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry a NUCP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that the NUCP transgene be integrated into the chromosomal site of the endogenous NUCP gene, gene targeting is preferred. Briefly, when such a technique is to be utilized, vectors containing some nucleotide sequences homologous to the endogenous NUCP gene are designed for the purpose of integrating, via homologous recombination with chromosomal sequences, into and disrupting the function of the nucleotide sequence of the endogenous NUCP gene (i.e., "knockout" animals).

The transgene may also be selectively introduced into a particular cell type, thus inactivating the endogenous NUCP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NUCP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NUCP gene-expressing tissue, may also be evaluated immunocytochemically using antibodies specific for the NUCP transgene product.

5.3. Antibodies to NUCPS

Antibodies that specifically recognize one or more epitopes of a NUCP, or epitopes of conserved variants of a NUCP, or peptide fragments of a NUCP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of a NUCP in a biological sample and may, therefore, be utilized as part of a diagnostic or prognostic technique whereby patients may be tested for abnormal amounts of a NUCP. Such antibodies may also be utilized in conjunction with, for example, compound screening schemes, as described below, for the evaluation of the effect of test compounds on expression and/or activity of a NUCP gene product. Additionally, such antibodies can be used in conjunction gene therapy to, for example, evaluate the normal and/or engineered NUCP-expressing cells prior to their introduction into the patient. Such antibodies may additionally be used as a method for inhibiting abnormally high NUCP activity. Thus, such antibodies may, therefore, be utilized as part of treatment methods.

For the production of antibodies, various host animals may be immunized by injection with a NUCP, a NUCP peptide (e.g., one corresponding the a functional domain of a NUCP), truncated NUCP polypeptides (a NUCP in which one or more domains have been deleted), functional equivalents of the NUCP or mutants of the NUCP. Such host animals may include but are not limited to rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NUCP gene products. Single chain antibodies are formed by linking the heavy and light chain fragments of the Fv region via an amino acid bridge, resulting in a single chain polypeptide.

Antibody fragments that recognize specific epitopes can be generated using known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NUCP can, in turn, be utilized to generate anti-idiotype antibodies that "mimic" a given NUCP, using techniques well known to those skilled in the art. (See, e.g., Greenspan & Bona, 1993, FASEB J 7(5):437–444; and Nissinoff, 1991, J. Immunol. 147(8):2429–2438). For example antibodies that bind to a NUCP domain and competitively inhibit the binding of a NUCP to its cognate ligand, chaperonin, or accessory molecule(s) can be used to generate anti-idiotypes that "mimic" the NUCP and, therefore, bind and activate or neutralize a receptor. Such anti-idiotypic antibodies or Fab fragments of such anti-idiotypes can be used in therapeutic regimens involving a NUCP-mediated process or pathway.

5.4. Diagnosis of Abnormalities Related to a NUCP

A variety of methods can be employed for the diagnostic and prognostic evaluation of disorders related to NUCP function, and for the identification of subjects having a predisposition to such disorders.

Such methods may, for example, utilize reagents such as the NUCP nucleotide sequences described above and the NUCP antibodies described above. Specifically, such reagents may be used, for example, for: (1) the detection of the presence of NUCP gene mutations, or the detection of either over- or under-expression of NUCP mRNA relative to a given phenotype; (2) the detection of either an over- or an under-abundance of NUCP gene product relative to a given phenotype; and (3) the detection of perturbations or abnormalities in any metabolic, physiologic, or catabolic pathway mediated by NUCP.

The methods described herein may be performed, for example, by utilizing pre-packaged diagnostic kits comprising at least one specific NUCP nucleotide sequence or NUCP antibody reagent described herein, which may be conveniently used, e.g., in clinical settings, to diagnose patients exhibiting, for example, body weight disorder abnormalities.

For the detection of NUCP mutations, any nucleated cell can be used as a starting source for genomic nucleic acid. For the detection of NUCP gene expression or NUCP gene products, any cell type or tissue in which the NUCP gene is expressed, such as, for example, kidney cells, may be utilized.

Nucleic acid-based detection techniques are described, below, in Section 5.4.1. Peptide detection techniques are described, below, in Section 5.4.2.

5.4.1. Detection of NUCP Sequences

Mutations within a NUCP nucleotide sequence can be detected by utilizing a number of techniques. Nucleic acid from any nucleated cell can be used as the starting point for such assay techniques, and can be isolated according to standard nucleic acid preparation procedures which are well known to those of skill in the art.

DNA may be used in hybridization or amplification assays of biological samples to detect abnormalities involving NUCP gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of NUCP gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described above, under conditions favorable for the specific annealing of these reagents to their complementary sequences within a NUCP gene. Preferably, the lengths of these nucleic acid reagents are at least about 15 to about 30 nucleotides. After incubation, all non-annealed nucleic acids are removed from the nucleic acid:NUCP molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining annealed, labeled NUCP nucleic acid reagents is accomplished using standard techniques well known to those in the art. The NUCP encoding nucleotide sequences to which the nucleic acid reagents have annealed can be compared to the annealing pattern expected from a normal NUCP gene sequence in order to determine whether a NUCP gene mutation is present.

Alternative diagnostic methods for the detection of NUCP gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of a NUCP gene in order to determine whether a NUCP gene mutation exists.

Additionally, well-known genotyping techniques can be performed to identify individuals carrying NUCP gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of NUCP gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the NUCP gene, and the diagnosis of diseases and disorders related to NUCP mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the NUCP gene, amplifying the extracted DNA, and labeling the repeat sequences to form a genotypic map of the individual's DNA.

The level of NUCP gene expression can also be assayed by detecting and measuring NUCP transcription. For example, RNA from a cell type or tissue known, or suspected to express the NUCP gene, such as kidney, may be isolated and tested utilizing hybridization or PCR techniques such as those described above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the NUCP gene. Such analyses may reveal both quantitative and qualitative aspects of the expression pattern of the NUCP gene, including activation or inactivation of NUCP gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the NUCP nucleic acid reagents described above. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining, by utilizing any other suitable nucleic acid staining method, or by sequencing.

Additionally, it is possible to perform such NUCP gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the NUCP gene.

5.4.2. Detection of NUCP Products

Antibodies directed against wild type or mutant NUCPs, or conserved variants or peptide fragments thereof, as discussed above, can also be used as diagnostics and prognostics, as described herein. Such diagnostic methods, may be used to detect abnormalities in the level of NUCP gene expression, or abnormalities in the structure and/or temporal, tissue, cellular, or subcellular location of the NUCP (besides mitochondria), and may be performed in vivo or in vitro, such as, for example, on biopsy tissue.

For example, antibodies directed to one or more epitopes of NUCP can be used in vivo to detect the pattern and level of expression of NUCP in the body. Such antibodies can be labeled, e.g., with a radio-opaque or other appropriate compound and injected into a subject in order to visualize binding to the NUCP expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier and permit labeling of NUCP expressed in the brain.

Additionally, any NUCP fusion protein or NUCP conjugated protein whose presence can be detected, can be administered. For example, NUCP fusion or conjugated proteins labeled with a radio-opaque or other appropriate compound can be administered and visualized in vivo, as discussed, above for labeled antibodies. Further such NUCP fusion proteins (such as AP-NUCP or NUCP-AP) can be utilized for in vitro diagnostic procedures.

Alternatively, immunoassays or fusion protein detection assays, as described above, can be utilized on biopsy and autopsy samples in vitro to permit assessment of the expression pattern of the NUCP. Such assays are not confined to the use of antibodies that define a NUCP domain, but can include the use of antibodies directed to epitopes of any domain of a NUCP. The use of each or all of these labeled antibodies will yield useful information regarding translation and intracellular transport of the NUCP to the cell surface and can identify defects in processing.

The tissue or cell type to be analyzed will generally include those which are known, or suspected, to express the NUCP gene, such as, for example, epithelial cells, kidney cells, adipose tissue, brain cells, etc. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the NUCP gene.

For example, antibodies, or fragments of antibodies, such as those described above useful in the present invention may be used to quantitatively or qualitatively detect the presence of a NUCP, or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such NUCP products can be found, at least transiently, on the cell surface.

The antibodies (or fragments thereof) or NUCP fusion or conjugated proteins useful in the present invention may additionally be employed histologically, as in immunofluorescence, immunoelectron microscopy or non-immuno assays, for in situ detection of NUCP gene products or conserved variants or peptide fragments thereof, or to assay NUCP binding (in the case of labeled NUCP-fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the NUCP product, or conserved variants or peptide fragments, or NUCP binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for a NUCP, or conserved variants or peptide fragments thereof, will typically comprise incubating a sample, such as a biological fluid, a tissue extract, freshly harvested cells, or lysates of cells which have been incubated in cell culture, in the presence of a detectably labeled antibody capable of identifying NUCP products or conserved variants or peptide fragments thereof, and detecting the bound antibody by any of a number of techniques well-known in the art. Alternatively, the labeled antibody can be directed against an antigenic tag that has been directly or indirectly attached to a NUCP.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled NUCP antibody or NUCP ligand/accessory molecule fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of NUCP antibody or NUCP ligand fusion protein may be determined according to well known methods. Those skilled in the art will be able to determine operative and optimal assay conditions for each determination by employing routine experimentation.

With respect to antibodies, one of the ways in which the NUCP antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme that is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect NUCP through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$EU, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.5. Screening Assays for Compounds that Modulate NUCP Expression or Activity

The following assays are designed to identify compounds that interact with (e.g., bind to) a NUCP, compounds that interfere with the interaction of a NUCP with any ligand or accessory molecules, compounds that modulate NUCP gene expression (i.e., modulate the level of NUCP activity by regulating gene expression) or otherwise modulate the levels of a NUCP in the body. Assays may additionally be utilized which identify compounds that bind to NUCP gene regulatory sequences (e.g., promoter sequences) and, consequently, may modulate NUCP gene expression. See e.g., Platt, K. A., 1994, J. Biol. Chem. 269:28558–28562, which is incorporated herein by reference in its entirety.

The compounds which can be screened in accordance with the invention include but are not limited to, peptides, antibodies and fragments thereof, and other organic compounds (e.g., peptidomimetics) that bind to NUCP and either mimic the activity of the natural product (i.e., agonists) or inhibit the activity of the natural ligand/accessory molecule (i.e., antagonists); as well as peptides, antibodies or fragments thereof, and other organic compounds that mimic the NUCP (or a portion thereof) and bind to and "inactivate" or "neutralize" the NUCP ligand/accessory protein.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds that can be screened in accordance with the invention include but are not limited to small organic molecules that are able to cross the blood-brain barrier, gain entry into an appropriate cell (e.g., in the choroid plexus, pituitary, the hypothalamus, etc.) and affect the expression of a NUCP gene or some other gene involved in a NUCP mediated pathway (e.g., by interacting with the regulatory region or transcription factors involved in gene expression); or such compounds that affect or substitute for the activity of the NUCP or the activity of some other intracellular factor involved in a NUCP-mediated catabolic, or metabolic pathway.

Computer modeling and searching technologies permit identification of compounds, or the improvement of already identified compounds, that can modulate NUCP expression or activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site (or binding site), either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential NUCP modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites (or binding sites) of NUCP, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Cell-based systems can also be used to identify compounds that bind (or mimic) NUCP as well as assess the altered activity associated with such binding in living cells. One tool of particular interest for such assays is green fluorescent protein which is described, inter alia, in U.S. Pat. No. 5,625,048, herein incorporated by reference. Cells that may be used in such cellular assays include, but are not limited to, leukocytes, or cell lines derived from leukocytes, lymphocytes, stem cells, including embryonic stem cells, and the like. In addition, expression host cells (e.g., B95 cells, COS cells, CHO cells, OMK cells, fibroblasts, Sf9 cells) genetically engineered to express a functional NUCP of interest and to respond to activation by the test, or natural, ligand, as measured by a chemical or phenotypic change, or induction of another host cell gene, can be used as an end point in the assay.

Compounds identified via assays such as those described herein may be useful, for example, in elucidating the biological function of NUCP. Such compounds can be administered to a patient at therapeutically effective doses to treat any of a variety of physiological or mental disorders. A therapeutically effective dose refers to that amount of the compound sufficient to result in any amelioration, impediment, prevention, or alteration of any biological symptom.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, intracranial, intrathecal, or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.5.1. In Vitro Screening Assays for Compounds that Bind to a NUCP

In vitro systems may be designed to identify compounds capable of interacting with (e.g., binding to) or mimicking a NUCP. The compounds identified can be useful, for example, in modulating the activity of wild type and/or mutant NUCP; can be useful in elaborating the biological function of NUCP; can be utilized in screens for identifying compounds that disrupt normal NUCP interactions; or may themselves disrupt or activate such interactions.

The principle of the assays used to identify compounds that bind to a NUCP, or NUCP ligands/accessory molecules, involves preparing a reaction mixture of NUCP and the test compound under conditions and for a time sufficient to allow the two components to interact and bind, thus forming a complex which can be removed and/or detected in the reaction mixture. The NUCP species used can vary depending upon the goal of the screening assay. For example, where agonists of a natural NUCP accessory molecule or ligand are desired, a full length NUCP, or a soluble truncated NUCP, a NUCP peptide, or NUCP fusion protein containing one or more NUCP domains fused to a protein or polypeptide that affords advantages in the assay system (e.g., labeling, isolation of the resulting complex, etc.) can be utilized. Where compounds that directly interact with a NUCP are sought, peptides corresponding to NUCP and fusion proteins containing a NUCP, or a portion thereof, can be used.

The screening assays can be conducted in a variety of ways. For example, one method to conduct such an assay would involve anchoring a NUCP, NUCP polypeptide, NUCP peptide, or fusion protein thereof, or the test substance onto a solid phase and detecting NUCP/test compound complexes anchored on the solid phase at the end of the reaction. In one embodiment of such a method, the NUCP reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a NUCP, NUCP polypeptide, peptide or fusion protein, or the test compound to anchor any complexes formed in solution, and a labeled antibody specific for the other component of the possible complex to detect anchored complexes.

Alternatively, cell-based assays can be used to identify compounds that interact with a NUCP. To this end, cell lines that express a NUCP, or cell lines (e.g., COS cells, CHO cells, fibroblasts, etc.) that have been genetically engineered to express a NUCP or a NUCP ligand/accessory molecule (e.g., by transfection or transduction of NUCP DNA, etc.) can be used. Interaction of the test compound with, for example, NUCP ligand expressed by the host cell can be determined by comparison or competition with native NUCP.

5.5.2. Assays for Compounds that Interfere with NUCP Receptor/Intracellular or NUCP/Transmembrane Macromolecule Interaction Macromolecules that interact with a NUCP are referred to, for purposes of this discussion, as "ebinding partners". These binding partners are likely to be involved in NUCP mediated biological pathways. Therefore, it is desirable to identify compounds that interfere with or disrupt the interaction of such binding partners which may be useful in regulating or augmenting NUCP activity in the body and/or controlling disorders associated with NUCP activity (or a deficiency thereof).

The basic principle of the assay systems used to identify compounds that interfere with the interaction between NUCP, or NUCP polypeptides, peptides or fusion proteins as described above (collectively, the NUCP moiety), and its binding partner or partners involves preparing a reaction mixture containing the NUCP moiety and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the NUCP moiety and its binding partner. Control reaction mixtures are incubated without the test compound or with a placebo. The formation of any complexes between the NUCP moiety and the binding partner is then detected. The formation of a complex in the control reaction, but not in the reaction mixture containing the test compound, indicates that the compound interferes with the interaction of the NUCP moiety and the interactive binding partner. Additionally, complex formation within reaction mixtures containing the test compound and normal NUCP may also be compared to complex formation within reaction mixtures containing the test compound and a mutant NUCP. This comparison may be important in those cases wherein it is desirable to identify compounds that specifically disrupt interactions of mutant, or mutated, NUCPs but not normal NUCPs.

The assay for compounds that interfere with the interaction of the NUCP moiety and its binding partners can be conducted in a heterogeneous or homogeneous format. Heterogeneous assays involve anchoring either the NUCP moiety or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to, or simultaneously with, the NUCP moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the NUCP moiety or an interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the NUCP moiety or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the NUCP moiety and an interactive binding partner is prepared in which either the NUCP moiety or its binding partners is labeled, but the signal generated by the label is quenched due to formation of the complex (see, e.g., U.S. Pat. No. 4,190,496 by Rubenstein which utilizes this approach for immunoassays). The addition of a test substance that competes with and displaces one of the species from the preformed complex will result in the generation of a signal above background. In this way, test substances which disrupt NUCP/intracellular binding partner interaction can be identified.

In a particular embodiment, a NUCP fusion can be prepared for immobilization. For example, NUCP or a peptide fragment can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and/or described above. This antibody can be labeled with the radioactive isotope $^{125}$I, for example, by methods routinely practiced in the art. In a heterogeneous assay, e.g., the GST-NUCP fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the NUCP moiety and the interactive binding partner can be detected by measuring the amount of radioactivity that remains associated with the glutathione-agarose beads. A successful inhibition of the interaction by the test compound will result in a decrease in measured radioactivity.

Alternatively, the GST-NUCP moiety fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the NUCP moiety/binding partner interaction can be detected by adding the labeled antibody and measuring the radioactivity associated with the beads.

In another embodiment of the invention, these same techniques can be employed using peptide fragments that correspond to the binding domain(s) of the NUCP moiety and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, the NUCP moiety can be anchored to a solid material as described, above, by making a GST-NUCP moiety fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-NUCP moiety fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. All patents, patent applications, and publications cited herein are hereby incorporated by reference.

What is claimed is:

1. A recombinant expression vector comprising an isolated nucleic acid molecule that encodes the amino acid sequence of SEQ ID NO:2.

2. The recombinant expression vector of claim 1, wherein said isolated nucleic acid molecule comprises the nucleic acid sequence of SEQ ID NO:1.

3. A host cell comprising the vector of claim 1.

4. A recombinant expression vector comprising an isolated nucleic acid molecule that encodes the amino acid sequence of SEQ ID NO:4.

5. The recombinant expression vector of claim 4, wherein said isolated nucleic acid molecule comprises the nucleic acid sequence of SEQ ID NO:3.

6. A host cell comprising the vector of claim 4.

* * * * *

SEQUENCE LISTING

<160> NUMBER OF SEQ ID NOS: 4

<210> SEQ ID NO 1
<211> LENGTH: 876
<212> TYPE: DNA
<213> ORGANISM: Homo sapiens

<400> SEQUENCE: 1

```
atgtcagccc tcaactggaa gccgtttgtg tacgggggc tggcctccat cactgctgag      60
tgcggtacat ttccaattga tttaaccaag acacggctcc agattcaagg ccagacgaat     120
gatgcaaaat ttaaggaaat tagataccga ggaatgttgc acgcattagt gaggataggc     180
agagaagaag ggctgaaagc actctactcg gggattgccc ccgcgatgtt acgccaggca     240
tcctatggca ccatcaagat aggcacttac cagagcttga agcgactatt cattgaacgc     300
ccagaagatg aaactctacc gataaatgtg atatgtggaa ttctgtctgg agtcatatct     360
tcaaccattg ctaatccaac tgatgttttg aaaattcgga tgcaagcgca aagcaacacc     420
attcaaggag gaatgatagg caacttcatg aacatttacc agcaagaggg gacaagagga     480
ctgtggaagg gtgtgtccct tactgcgcag agggctgcta ttgttgttgg tgtggagctg     540
ccggtctatg acatcaccaa gaagcatctt attctctcag gcctgatggg agacactgtg     600
tatacccact tcctctcaag cttcacctgt ggtctggcag gggccctggc ctcaaaccct     660
gttgatgttg tgaggacacg tatgatgaat cagagagtgc ttcgagatgg cagatgttct     720
ggctacacag gaaccctgga ttgcttgtta cagacatgga agaatgaagg gttttttgct     780
```

```
ctctataaag cttttggcc aaattggttg agacttggtc cttggaatat catttctttt    840
gtgacatacg agcagttgaa gaaattggat ttgtga                              876
```

<210> SEQ ID NO 2
<211> LENGTH: 291
<212> TYPE: PRT
<213> ORGANISM: Homo sapiens

<400> SEQUENCE: 2

```
Met Ser Ala Leu Asn Trp Lys Pro Phe Val Tyr Gly Gly Leu Ala Ser
  1               5                  10                  15

Ile Thr Ala Glu Cys Gly Thr Phe Pro Ile Asp Leu Thr Lys Thr Arg
             20                  25                  30

Leu Gln Ile Gln Gly Gln Thr Asn Asp Ala Lys Phe Lys Glu Ile Arg
         35                  40                  45

Tyr Arg Gly Met Leu His Ala Leu Val Arg Ile Gly Arg Glu Glu Gly
     50                  55                  60

Leu Lys Ala Leu Tyr Ser Gly Ile Ala Pro Ala Met Leu Arg Gln Ala
 65                  70                  75                  80

Ser Tyr Gly Thr Ile Lys Ile Gly Thr Tyr Gln Ser Leu Lys Arg Leu
                 85                  90                  95

Phe Ile Glu Arg Pro Glu Asp Glu Thr Leu Pro Ile Asn Val Ile Cys
            100                 105                 110

Gly Ile Leu Ser Gly Val Ile Ser Ser Thr Ile Ala Asn Pro Thr Asp
        115                 120                 125

Val Leu Lys Ile Arg Met Gln Ala Gln Ser Asn Thr Ile Gln Gly Gly
    130                 135                 140

Met Ile Gly Asn Phe Met Asn Ile Tyr Gln Gln Glu Gly Thr Arg Gly
145                 150                 155                 160

Leu Trp Lys Gly Val Ser Leu Thr Ala Gln Arg Ala Ala Ile Val Val
                165                 170                 175

Gly Val Glu Leu Pro Val Tyr Asp Ile Thr Lys Lys His Leu Ile Leu
            180                 185                 190

Ser Gly Leu Met Gly Asp Thr Val Tyr Thr His Phe Leu Ser Ser Phe
        195                 200                 205

Thr Cys Gly Leu Ala Gly Ala Leu Ala Ser Asn Pro Val Asp Val Val
    210                 215                 220

Arg Thr Arg Met Met Asn Gln Arg Val Leu Arg Asp Gly Arg Cys Ser
225                 230                 235                 240

Gly Tyr Thr Gly Thr Leu Asp Cys Leu Leu Gln Thr Trp Lys Asn Glu
                245                 250                 255

Gly Phe Phe Ala Leu Tyr Lys Gly Phe Trp Pro Asn Trp Leu Arg Leu
            260                 265                 270

Gly Pro Trp Asn Ile Ile Phe Phe Val Thr Tyr Glu Gln Leu Lys Lys
        275                 280                 285

Leu Asp Leu
    290
```

<210> SEQ ID NO 3
<211> LENGTH: 882
<212> TYPE: DNA
<213> ORGANISM: Homo sapiens

<400> SEQUENCE: 3

```
atgtcagccc tcaactggaa gccgtttgtg tacggggggc tggcctccat cactgctgag    60
```

```
tgcggtacat ttccaattga tttaaccaag acacggctcc agattcaagg ccagacgaat      120
gatgcaaaat ttaaggaaat tagataccga ggaatgttgc acgcattagt gaggataggc      180
agagaagaag ggctgaaagc actctactcg gggattgccc ccgcgatgtt acgccaggca      240
tcctatggca ccatcaagat aggcacttac cagagcttga agcgactatt cattgaacgc      300
ccagaagata aaactctacc gataaatgtg atatgtggaa ttctgtctgg agtcatatct      360
tcaaccattg ctaatccaac tgatgttttg aaaattcgga tgcaagcgca aagcaacacc      420
attcaaggag gaatgatagg caacttcatg aacatttacc agcaagaggg gacaagagga      480
ctgtggaagg gtgtgtccct tactgcgcag agggctgcta ttgttgttgg tgtggagctg      540
ccggtctatg acatcaccaa gaagcatctt attctctcag gcctgatggg agacactgtg      600
tatacccact tcctctcaag cttcacctgt ggtctggcag gggccctggc ctcaaaccct      660
gttgatgttg tgaggacacg tatgatgaat cagagagtgc ttcgagatgg cagatgttct      720
ggctacacag gaaccctgga ttgcttgtta cagcttacag tgctggaaag ttttccacc       780 acagcaaagc cacaaaagct tatcagcgta gatgccatct cagaagaggc tgataccagg      840
ggatttacat atctcagctg tgatctttct gctccaagct ga                         882
```

<210> SEQ ID NO 4
<211> LENGTH: 293
<212> TYPE: PRT
<213> ORGANISM: Homo sapiens

<400> SEQUENCE: 4

```
Met Ser Ala Leu Asn Trp Lys Pro Phe Val Tyr Gly Gly Leu Ala Ser
 1               5                   10                  15

Ile Thr Ala Glu Cys Gly Thr Phe Pro Ile Asp Leu Thr Lys Thr Arg
            20                  25                  30

Leu Gln Ile Gln Gly Gln Thr Asn Asp Ala Lys Phe Lys Glu Ile Arg
        35                  40                  45

Tyr Arg Gly Met Leu His Ala Leu Val Arg Ile Gly Arg Glu Glu Gly
    50                  55                  60

Leu Lys Ala Leu Tyr Ser Gly Ile Ala Pro Ala Met Leu Arg Gln Ala
65                  70                  75                  80

Ser Tyr Gly Thr Ile Lys Ile Gly Thr Tyr Gln Ser Leu Lys Arg Leu
                85                  90                  95

Phe Ile Glu Arg Pro Glu Asp Glu Thr Leu Pro Ile Asn Val Ile Cys
            100                 105                 110

Gly Ile Leu Ser Gly Val Ile Ser Ser Thr Ile Ala Asn Pro Thr Asp
        115                 120                 125

Val Leu Lys Ile Arg Met Gln Ala Gln Ser Asn Thr Ile Gln Gly Gly
    130                 135                 140

Met Ile Gly Asn Phe Met Asn Ile Tyr Gln Gln Glu Gly Thr Arg Gly
145                 150                 155                 160

Leu Trp Lys Gly Val Ser Leu Thr Ala Gln Arg Ala Ala Ile Val Val
                165                 170                 175

Gly Val Glu Leu Pro Val Tyr Asp Ile Thr Lys Lys His Leu Ile Leu
            180                 185                 190

Ser Gly Leu Met Gly Asp Thr Val Tyr Thr His Phe Leu Ser Ser Phe
        195                 200                 205

Thr Cys Gly Leu Ala Gly Ala Leu Ala Ser Asn Pro Val Asp Val Val
    210                 215                 220
```

-continued

```
Arg Thr Arg Met Met Asn Gln Arg Val Leu Arg Asp Gly Arg Cys Ser
225                 230                 235                 240

Gly Tyr Thr Gly Thr Leu Asp Cys Leu Leu Gln Leu Thr Val Leu Glu
            245                 250                 255

Ser Phe Ser Thr Thr Ala Lys Pro Gln Lys Leu Ile Ser Val Asp Ala
            260                 265                 270

Ile Ser Glu Glu Ala Asp Thr Arg Gly Phe Thr Tyr Leu Ser Cys Asp
        275                 280                 285

Leu Ser Ala Pro Ser
        290
```